United States Patent
Razavi

(10) Patent No.: US 9,474,881 B2
(45) Date of Patent: Oct. 25, 2016

(54) SHEATH AND METHOD OF USE

(76) Inventor: Mehdi Razavi, Houston, TX (US)

( * ) Notice: Subject to any disclaimer, the term of this patent is extended or adjusted under 35 U.S.C. 154(b) by 1463 days.

(21) Appl. No.: 13/160,219

(22) Filed: Jun. 14, 2011

(65) Prior Publication Data

US 2011/0306970 A1 Dec. 15, 2011

Related U.S. Application Data

(60) Provisional application No. 61/354,344, filed on Jun. 14, 2010.

(51) Int. Cl.
*A61B 18/18* (2006.01)
*A61M 25/06* (2006.01)
*A61B 18/14* (2006.01)
*A61B 18/00* (2006.01)
*A61B 18/02* (2006.01)

(52) U.S. Cl.
CPC ....... *A61M 25/0662* (2013.01); *A61B 18/1492* (2013.01); *A61B 2018/00029* (2013.01); *A61B 2018/00166* (2013.01); *A61B 2018/00363* (2013.01); *A61B 2018/0212* (2013.01); *A61B 2218/007* (2013.01); *A61M 2025/0681* (2013.01)

(58) Field of Classification Search
CPC ............... A61B 18/1492; A61B 2018/00029; A61B 2018/00166; A61B 2018/00363; A61B 2018/0212; A61B 2218/007; A61M 2025/0681; A61M 25/0662
USPC ....................................... 606/35–48
See application file for complete search history.

(56) References Cited

U.S. PATENT DOCUMENTS

| | | | |
|---|---|---|---|
| 5,122,138 A * | 6/1992 | Manwaring | 606/46 |
| 5,197,963 A * | 3/1993 | Parins | 606/46 |
| 5,733,323 A * | 3/1998 | Buck et al. | 607/122 |
| 6,063,081 A * | 5/2000 | Mulier et al. | 606/45 |
| 6,235,021 B1 | 5/2001 | Sieben | |
| 6,960,205 B2 * | 11/2005 | Jahns et al. | 606/41 |
| 8,323,280 B2 * | 12/2012 | Germain et al. | 606/49 |
| 2005/0177151 A1 | 8/2005 | Coen et al. | |
| 2005/0183954 A1 * | 8/2005 | Hitchcock et al. | 204/403.01 |
| 2005/0251133 A1 * | 11/2005 | Jahns et al. | 606/41 |
| 2006/0074410 A1 * | 4/2006 | Malecki et al. | 606/32 |

* cited by examiner

*Primary Examiner* — Michael Peffley
*Assistant Examiner* — Amanda Zink
(74) *Attorney, Agent, or Firm* — Trop, Pruner & Hu, P.C.

(57) ABSTRACT

In an embodiment a sheath allows one to simultaneously ablate tissue, using a catheter located in the sheath, and remove fluid from a patient's pericardial space, via the same sheath, all without withdrawing the ablation catheter from the sheath. Applying pressure (positive or negative) to fenestrations in the sheath may allow one to withdraw fluid from the space, navigate the sheath within the space, and/or adhere the sheath to tissue in the space. Other embodiments are described herein.

18 Claims, 5 Drawing Sheets

SHEATH AND METHOD OF USE

This application claims priority to U.S. Provisional Patent Application No. 61/354,344 filed on Jun. 14, 2010 and entitled "Sheath and Method of Use," the content of which is hereby incorporated by reference.

BACKGROUND

Pericardial access for cardiac ablation is often accompanied by the need to place a sheath in or around the pericardial space. A radiofrequency (RF) ablation catheter may be deployed in the sheath. The sheath may also provide for irrigation. The purposes of such irrigation may include, but are not limited to, controlling localized temperature increases to thereby allow the delivery of deeper lesions.

It follows that during pericardial ablation, fluid may accumulate inside the pericardium to an undesirable degree. Furthermore, accumulation of pericardial fluid may be from other causes not related to irrigation from the sheath. These include, but are not limited to, irritation in the pericardial space causing increased pericardial fluid product, application of cryoablative energy that increases fluid volume in the pericardial space, or bleeding as a complication of perforation of either the epicardial coronary vessels or of the cardiac chambers.

Accordingly, pericardial ablation may involve removing accumulated fluid by any of various methods. First, fluid removal may be performed by removing the ablation catheter, inserting another catheter into the sheath, and then removing the fluid via the second catheter. Second, fluid may also be removed by utilizing the space around the ablation catheter. The first method of removing fluid requires multiple withdrawals and reinsertions of the ablation catheter. The second method of removing fluid is limited by a markedly limited amount of residual lumen (in the sheath) that is available for fluid flow in addition to holding the ablation catheter. Thus, there is limited capability to remove fluid while the ablation catheter is in place. Furthermore, use of a sheath that is "oversized" relative to the ablation catheter is clinically unwise during pericardial access. This is true because such sheathes require a larger puncture considering the sheath must have a greatly enlarged diameter to allow any appreciable fluid flow about the catheter.

BRIEF DESCRIPTION OF THE DRAWINGS

Features and advantages of embodiments of the present invention will become apparent from the appended claims, the following detailed description of one or more example embodiments, and the corresponding figures, in which:

DETAILED DESCRIPTION

In the following description, numerous specific details are set forth but embodiments of the invention may be practiced without these specific details. Well-known circuits, structures and techniques have not been shown in detail to avoid obscuring an understanding of this description. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical or electrical contact. While similar or same numbers may be used to designate same or similar parts in different figures, doing so does not mean all figures including similar or same numbers constitute a single or same embodiment.

In an embodiment a sheath allows one to simultaneously ablate tissue, using a catheter located in the sheath, and remove fluid from a patient's pericardial space, via the same sheath, all without withdrawing the ablation catheter from the sheath. Applying pressure (positive or negative) to fenestrations in the sheath may allow one to withdraw fluid from the space, navigate the sheath within the space, and/or adhere the sheath to tissue in the space.

As used herein, "simultaneous" does not necessarily mean actions must start and stop simultaneously. Rather, such actions may instead include starting and/or stopping at different times but with some period of overlap when both actions are occurring.

Figure 1A:
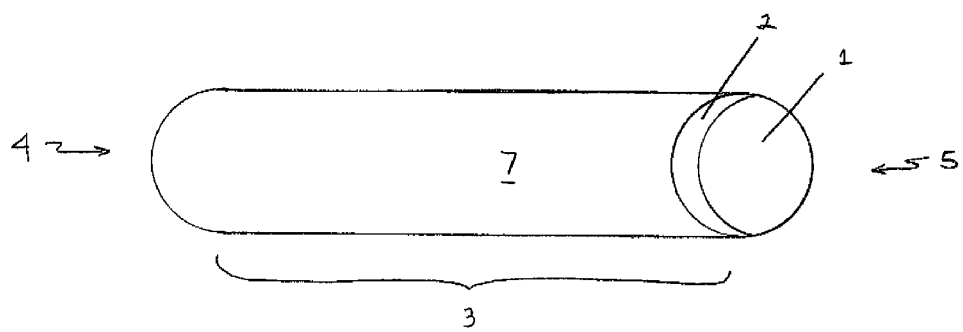
FIGS. 1A and 1B include a sheath in an embodiment of the invention.
Figure 1B:
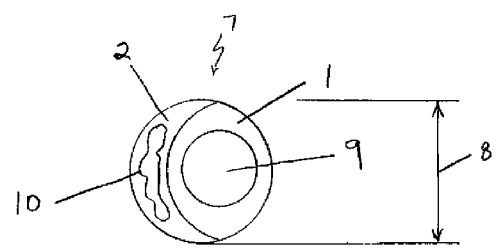

FIGS. 1A and 1B include sheath 7 in an embodiment of the invention. In FIG. 1A, first lumen 1 and second lumen 2 are shown in the long axis 3 of sheath 7. Distal end 4 and proximal end 5 of sheath 7 are noted. Lumens 1 and 2 may be of variable length with regards to each other. For example, lumen 2 may terminate anywhere before proximal end 5 of sheath 7 and/or distal end 4 of sheath 7.

FIG. 1B shows short axis 8 of first lumen 1 and second lumen 2. Lumens may be adjacent one another, one lumen located inside another lumen, and the like. In one embodiment, catheter 9 is included in first lumen 1. Catheter 9 may be an ablation catheter (e.g., RF ablation, cryo ablation, and the like), electrocardiogram (ECG) sensing catheter, pressure catheter, and the like. Lumen 2 may provide a conduit to supply and/or remove fluid 10.

Figure 2:
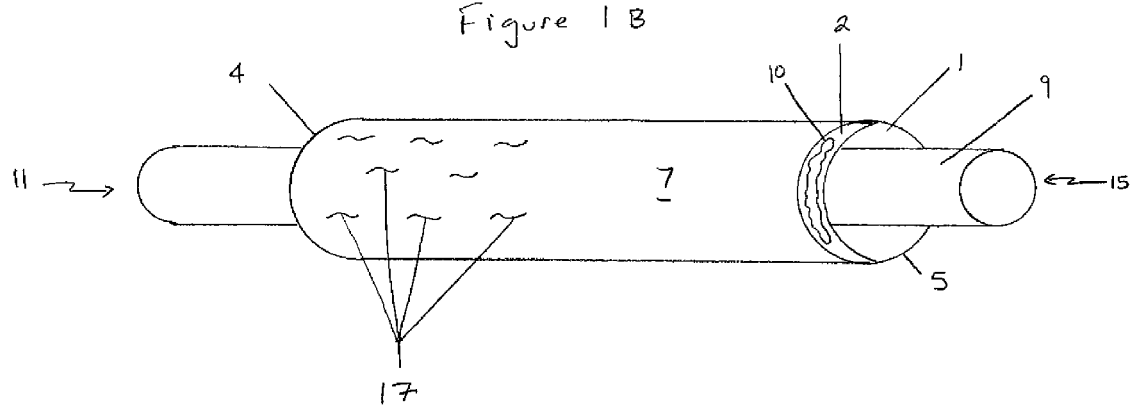
FIG. 2 includes a sheath in an embodiment of the invention.

FIG. 2 includes sheath 7 in an embodiment of the invention. Distal end 4 and proximal end 5 of sheath 7 are noted. Catheter 9 is included in first lumen 1. Catheter 9 may include proximal and distal ends 15 and 11 respectively. Distal end 11 of catheter 9 is shown extruding through the distal end 4 of sheath 7. Lumen 2 may provide a conduit to supply and/or remove fluid 10. Second lumen 2 may be drained or irrigated using, for example, a syringe (not shown) coupled to second lumen 2. Fluid may enter or exit second lumen 2 via one or more fenestrations 17 (i.e., windows or openings) located in a side wall of sheath 7.

Figure 7:
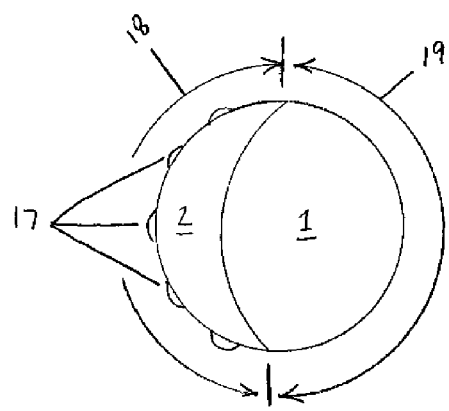
FIG. 7 includes a sheath in an embodiment of the invention.

As seen in FIG. 7, in an embodiment multiple fenestrations 17 are included in second lumen 2. As shown, first and second lumens are located adjacent one another such that lumen 1 shares an outside wall portion 19 of the sheath and lumen 2 also includes an outside wall portion 18 of the sheath. Fenestrations 17 may not encircle the entire sheath (at least at the cross section of FIG. 7) but may be limited to one area, such as the outer side wall for lumen 2.

Figure 8:
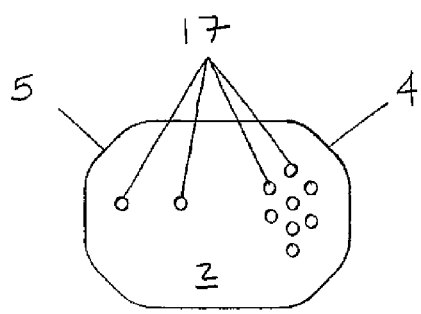
FIG. 8 includes a sheath in an embodiment of the invention.

As shown in FIG. 8, staggering fenestrations may help steer and/or stabilize the sheath at various locations. For example, fenestrations 17 are more concentrated near distal end 4 of second lumen 2 than proximal end 5 of second lumen 2. Doing so may concentrate suction and/or irrigation near distal end 4, which may be located closest to an ablation site that is has relatively higher needs for irrigation and/or fluid removal. Thus, fluid may be removed/added more quickly near end 4 due to the greater concentration and surface area of fenestrations near end 4. In an embodiment (not shown), fenestrations may go around the entire sheath circumference in some locations but not at other locations.

Figure 3:
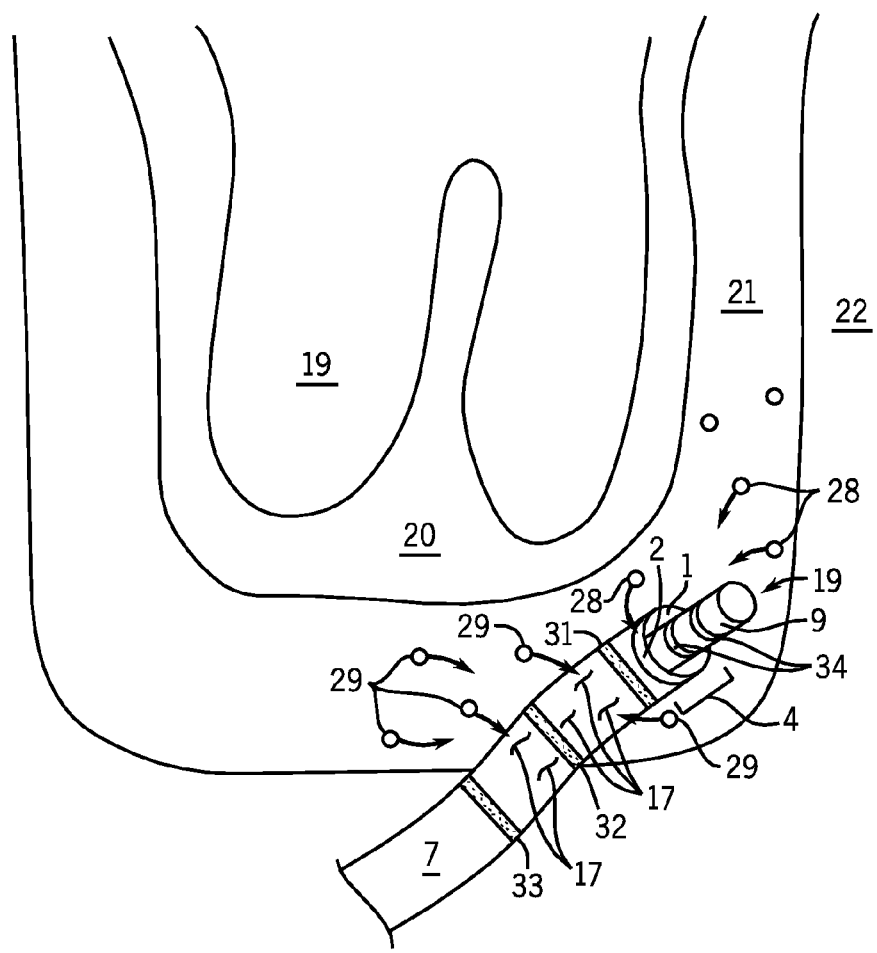
FIG. 3 includes a sheath in an embodiment of the invention.

FIG. 3 demonstrates an embodiment as it traverses the pericardium. The internal cavity 19 of the heart and the heart muscle 20 itself is surrounded by pericardium 22. Pericardial space 21 is accessed by sheath 7 with its first lumen 1 and second lumen 2. Ablation catheter 9 is introduced into the pericardial space via first lumen 1. Distal end 19 of ablation catheter 9 includes an electrode that is exposed in the pericardial space to perform ablation. Ablation catheter 9 may include sensing electrodes 34. Fluid, blood, or any other liquid 28, 29 (e.g., liquid created as a consequence of any part of procedure) is suctioned (e.g., based on negative pressure from a syringe or other active or passive means) via second lumen 2. Fluid 28 is returned via second lumen 2 from an opening at the distal end 4 of the sheath. Other fluid 29 is returned via fenestrations 17 on a free wall (i.e., wall not in full contact with tissue) of second lumen 2. The arrows demonstrate the flow of fluid 28, 29 from the pericardial space 21, to second lumen 2 (which may be coupled to, for example, a syringe (not shown)).

Figure 6:
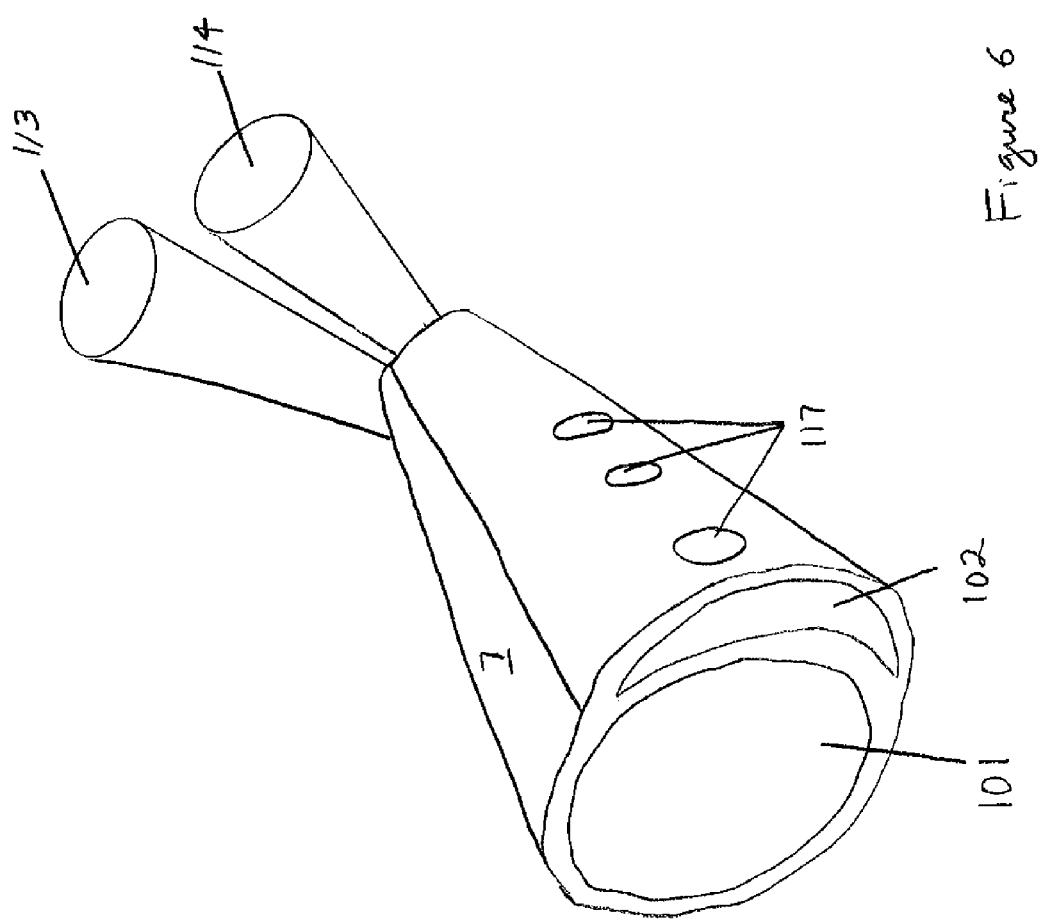
FIG. 6 includes a sheath in an embodiment of the invention.

FIG. 6 includes in an embodiment where cones 113, 114 represent suction ports in sheath 7. Port 113 drains/irrigates lumen 102 and port 114 drains/irrigates lumen 101 (which may also accommodate a catheter). Lumen 102 includes fenestrations 117.

Figure 5:
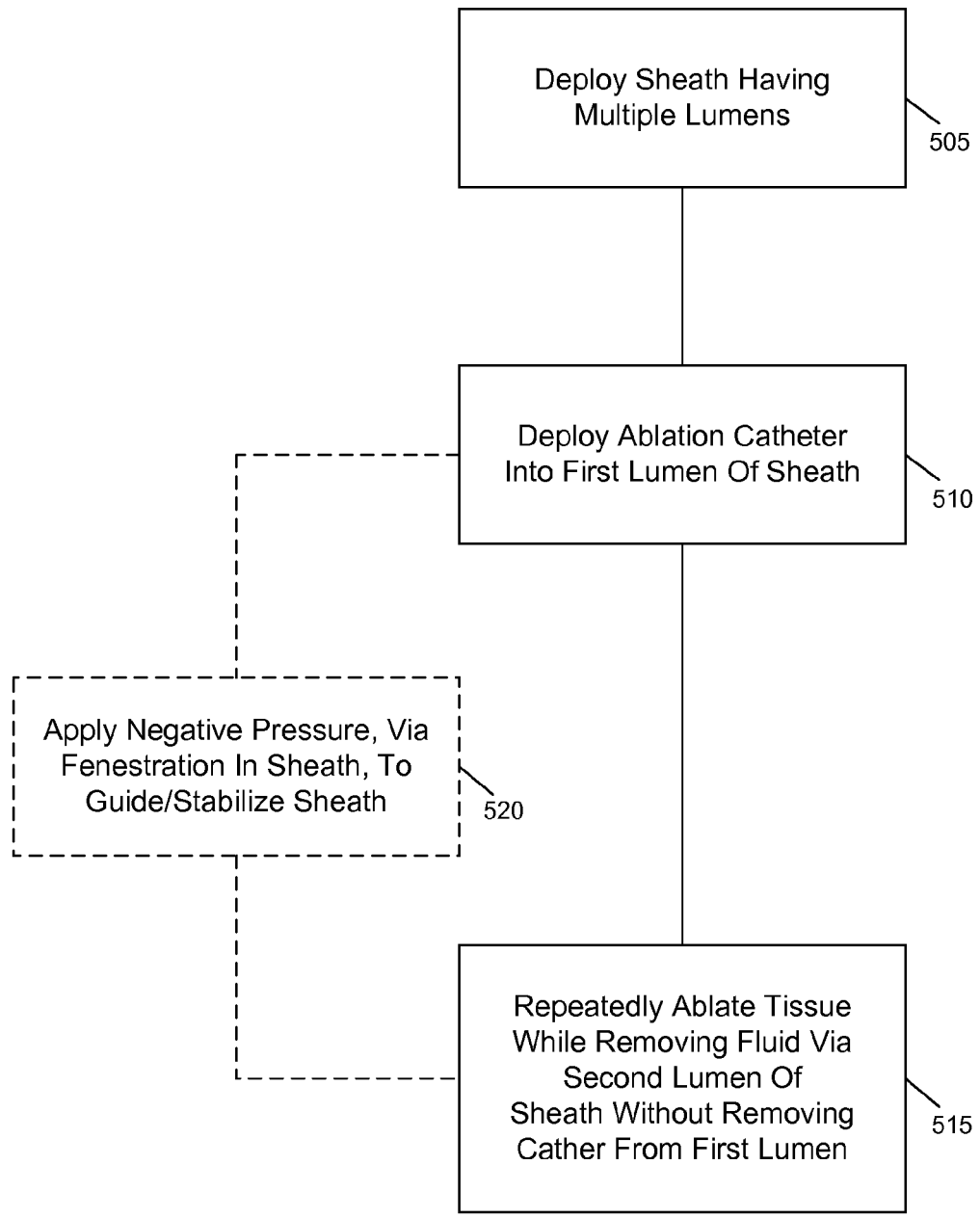
FIG. 5 includes a method in an embodiment of the invention.

FIG. 5 includes method 500 in an embodiment of the invention.

Block 505 includes providing a sheath having multiple lumens (e.g., first and second lumens). Block 510 includes deploying a catheter (e.g., ablation catheter) within the first lumen. Block 515 includes ablating patient tissue with the catheter; and removing patient fluid via the second lumen without removing the catheter from the first lumen. In an embodiment, the ablation and fluid removal occur simultaneously but other embodiments are not so restricted.

As one example, block 515 may concern a method including: (a) ablating tissue with the catheter; then (b) removing the fluid via the second lumen; and then (c) ablating additional tissue with the catheter. Steps (a), (b), and (c) may be performed sequentially (one after the other) without removing the catheter from the first lumen during or between any of steps (a), (b), and (c). Thus, the physician does not need to delicately locate the catheter at the ablation site, ablate, then remove the catheter in order to insert another catheter to remove fluid (or remove the ablation catheter to provide room in the sheath to remove fluid), then painstakingly relocate the ablation catheter to make a second ablation.

Block 520 is included in a dashed line format to indicate the block is an option for an embodiment of method 500. For example, the embodiment may include stabilizing the sheath against tissue by applying negative pressure, relative to pressure inside the patient's body nearby the catheter, to a fenestration included in the sheath. In other words, "negative pressure" does not necessarily mean relative to atmosphere but more practically relative the internal environment generally nearby opening of the sheath when the sheath is in the patient. Thus, the negative pressure will draw fluid into the sheath for fluid removal. However, when fenestrations are located adjacent tissue the use of suction may act to fix or localize the sheath against tissue (e.g., heart wall, pericardium, and the like). Such stabilization may make ablating at key locations more easy to accomplish.

For example, an embodiment of the invention includes a sheath with first and second fenestrations included entirely between, but separate from, the proximal and distal ends of the sheath. For example, the fenestrations are included in a side wall of the sheath. A method may include applying negative pressure to the first fenestration but not the second fenestration. This may result in drawing fluid into the first fenestration but not the second fenestration. It may include adhering the first fenestration area to tissue (i.e., stabilization of sheath) but not the area near the second fenestration. It may include navigating the sheath within a space (e.g., the pericardial space) by applying the pressure to one fenestration but not another. Doing so may deflect an area of the sheath (i.e., the area around the fenestration). If the fenestration is near the distal end of the sheath then applying negative pressure to the fenestration may deflect the end of the sheath towards the fenestration.

In a similar manner, irrigating through one fenestration but not another may deflect a portion of the sheath (e.g., near the distal end of the sheath) away from the fenestration. Also, the distal end of a fluid lumen (e.g., lumen 2 of FIG. 1) may be sealed to concentrate fluid pressure (e.g., negative (suction) or positive (irrigation)) through side wall fenestrations (instead of allowing some pressure to be directed towards a window at the distal end of the lumen). For example, FIG. 4 includes an embodiment with fenestrations on opposing sides of a sheath. Using different lumens 402, 403 pressure (positive or negative) could be applied to some fenestrations (e.g., 417) but not others (e.g., 418).

Figure 4:
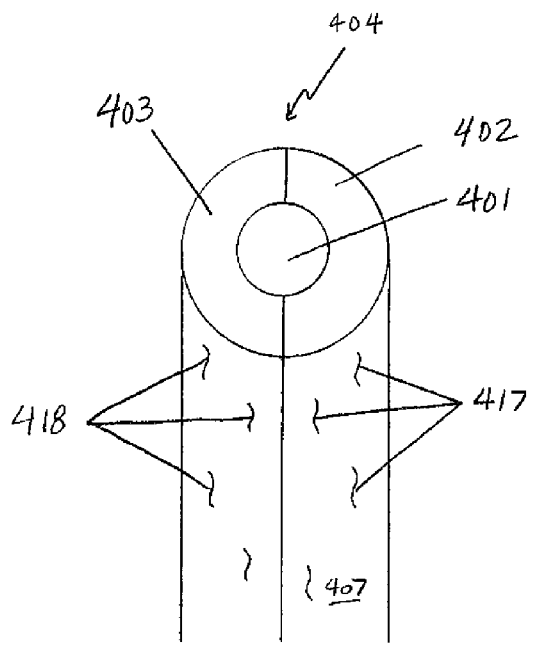
FIG. 4 includes a sheath in an embodiment of the invention.

In contrast to FIG. 4, FIG. 6 includes an embodiment wherein fenestrations are located along just one side of the sheath. Thus, to navigate the sheath in a one direction but not the other direction, positive or negative pressure may be applied to guide the sheath away or towards fenestrations 117. Also, sheath 7 may be rotated about its long axis to vary the direction of fenestrations 117 and thereby vary the effect of the positive/negative pressure applications to fenestrations 117.

In an embodiment pressure (positive or negative) may be alternately applied to one fenestration and then another. In an embodiment with fenestrations on opposing sheath side walls, doing this alternating pressure application may "snake" or "wiggle" the sheath along a path. The snaking advancement may possibly be aided (to varying degrees) by forward force supplied by the user (e.g., physician).

Of note, when fluid is suctioned by the second lumen a "potential" space may exist through which the catheter/sheath may be drawn. To that end, stabilizing and/or navigating "suction" tips for the pericardium are described. For example, application of negative force through the "second" manifold/handle of a sheath (connected to the draining lumen and fenestrations) will apply negative force that, via the increased surface area of the fenestrations, will enable stabilization of the sheath against the pericardium. In an embodiment a distal aspect of the sheath may, on the free edge (i.e., not the septum) of the second lumen, have side opening ports (e.g., FIG. 6). These side ports may allow the sheath, either by suction or a mechanical device passed distally via the lumen, to temporarily grip or adhere to adjacent tissue, such as epicardial tissue. Thus, the sheath is releaseably stabilized (e.g., via suction) for a period of time in a desired location or position. Suction may occur via side ports and/or a distal port on the distal end of the sheath.

Suction may be applied simultaneously or non-simultaneously to any of the combination of ports using various lumens. For example, suction to one set of side ports may help adhere the sheath to one location while still providing suction of fluids via the distal end and/or other side ports. Some side ports may provide for suction while other side ports are disconnected from negative pressure (relative to pressure inside body near catheter) to avoid adhering the second group of ports to tissue (which may avoid frustrating sheath location efforts of the user). The use of varied suction ports and/or negative pressures may help steer and/or stabilize the sheath at various locations (e.g., supplying negative pressure at one location but not another).

Thus, in an embodiment a method allows one to repeatedly, without removing the catheter from the first lumen, both (a) ablate tissue with a catheter; and (b) remove fluid and/or navigate the catheter via positive and/or negative pressure applied via the second lumen. The ablated tissue may be located in the pericardial space (or elsewhere), where navigating a catheter can be troublesome and where cooling an ablation catheter can also be troublesome.

One embodiment includes monitoring a cardiac biosignal via an electrode fixedly connected to the sheath and separate from the catheter. For example, in FIG. 3 an embodiment of sheath 7 may have electrodes 31, 32, 33 imbedded along its length. These electrodes may allow the operator to, for example, determine the location of the distal aspect of the sheath via cardiac electrogram. This may enhance targeting locations of interest.

One embodiment includes simultaneously (a) ablating tissue with the catheter, (b) removing fluid via the second lumen, and (c) irrigating an area near the tissue being ablated. For example, with FIG. 4 fluid may be excreted via fenestrations 418 at a first rate and removed via fenestrations 417 at a second rate. The first and second rates may be unequal. For example, during active ablation fluid may be added at a higher rate than the fluid is withdrawn in order to help tissue cooling. A distal port may be open for the same lumen that is adding fluid (e.g., lumen 403), while the distal port for the lumen that is removing fluid (e.g., lumen 402) may be closed. Doing so may help ensure added fluid is not removed too quickly.

As shown herein, various embodiments may include a sheath which enables simultaneous placement, manipulation, and use of catheters to a region. Such embodiments may use two lumens to locate a catheter at a region while also adding fluid to the same region, and even removing fluid (e.g., by suction or gravitation) through the same sheath. However, other embodiments may use other lumen scenarios. For example, in FIG. 4 lumen 401 is located within lumens 403 and 402. A catheter may occupy lumen 401. Irrigation may occur via lumen 403 while fluid suction occurs via lumen 402. Such fluid flow may occur via fenestrations 418, 417 and or voids at the distal end 404 of the sheath. Irrigation and fluid removal may occur simultaneously. Such irrigation and fluid removal may occur while (e.g., simultaneously) ablation occurs via a catheter located in (at least partially) lumen 401.

In an embodiment, each lumen may have a single opening at some location at or near the distal end on the sheath. In other embodiments, each of the lumens may have multiple holes or fenestrations along the sheath. Also, each of lumens may have both fenestrations and a final, terminal opening or port. These openings may be side-facing (relative to the sheath's long axis), or may be aligned with the long axis of the sheath. The separate lumens may be separated by septum (s) that also may or may not be fenestrated. One or more lumens, on or around the lumen's proximal end, may connect to a stopcock, tubing, manifold, or other mechanism which may then connect to a pump, syringe, or other device that will allow active (e.g., by continuous or non-continuous suction or vacuum pumping) or passive (e.g., by force of gravity) removal and/or collection of fluid at a variable rate selected by a user based on clinical circumstances. Similarly, one or more lumens may be attached proximally to a system for the delivery and control of irrigation distally. The target location may or may not be the pericardial space (as this invention may also be utilized for other spaces).

In an embodiment a distal aspect of a sheath will, on the free edge (i.e., not the septum) of the second lumen, have fenestrations. These fenestrations may traverse a distance ranging 1, 3, 6, 9, 12, 15, 18, 21, 24 centimeters (and so on) from the distal end and towards the proximal end of the sheath. These fenestrations will facilitate exposure of the sheath to any exposed fluid, thus facilitating the removal of fluid via the second lumen. For example, the pericardial space may be a potential space (i.e., locations with pressure differentials) with limited size. Fluid pockets or the location of fluid may limit exposure of the distal end of the sheath to fluid that needs to be removed. The fenestrations may provide increased exposure to any such fluid, thus facilitating its removal via the second lumen.

In an embodiment a wire, second catheter, and the like may be introduced through the second lumen. The wire or second catheter may increase positional stability of the sheath.

In various embodiments, the suction, irrigation, or both may be continuous and generated by a pump mechanism. In various embodiments, the irrigation and suction may be simultaneous or may be serially intermittent as desired by the operator for different clinical procedures. Likewise, RF ablation and the suction may be simultaneous or may be serially intermittent as desired by the operator for different clinical procedures.

In various embodiments, the body of the sheath may be in the range of 20 to 110 cm in length (but may also be longer or shorter). The body of the sheath may be in the range of 1 to 12 French in diameter (but may be thicker or thinner).

The device features described herein may be variously combined to add clinical flexibility to a method of using a sheath to facilitate access to a desired body region for at least one or more therapeutic and/or diagnostic catheters while simultaneously enabling irrigation, suction, and/or location or position stabilization of the sheath and catheters.

While at times embodiments have been described in terms of a sheath for pericardial access and ablation, embodiments are not limited to pericardial access and therapy. Embodiments apply to similar sheaths where the combination of facilitating access to a desired body region for one or more therapeutic and/or diagnostic catheters while simultaneously enabling irrigation, suction, and/or location or position stabilization of the sheath and catheters is desirable. Such uses exist in, for example, urology, pulmonology, proctology, gastrology, gynecology, and other specialties of medical practice.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. A method comprising:
providing a sheath having first and second lumens and first and second fenestrations, wherein the first and second fenestrations are included entirely between, but separate from, proximal and distal ends of the sheath;
deploying a catheter within the first lumen;
applying negative pressure to the first fenestration but not the second fenestration;
applying negative pressure to the second fenestration but not the first fenestration;
ablating patient tissue with the catheter; and
removing patient fluid via the second lumen while the catheter is deployed within the first lumen.

2. The method of claim 1 including simultaneously performing: (a) the ablating the patient tissue with the catheter and (b) the removing the patient fluid via the second lumen.

3. The method of claim 1 including stabilizing the sheath against the patient tissue by applying negative pressure to at least one of the first and second fenestrations.

4. The method of claim 1 comprising again ablating the patient tissue with the catheter; wherein: (a) the ablating the patient tissue with the catheter; (b) the removing the patient fluid via the second lumen; and (c) the again ablating the patient tissue with the catheter are performed without removing the catheter from the first lumen during or between any of the ablating the patient tissue with the catheter, the removing the patient fluid via the second lumen, and the again ablating the patient tissue with the catheter.

5. The method of claim 1 including irrigating an area near the patient tissue via the second lumen.

6. The method of claim 1, wherein:
the second lumen includes multiple fenestrations including two or more of the first fenestration, the second fenestration, and additional fenestrations;
the removing the patient fluid via the second lumen includes removing the patient fluid via the multiple fenestrations.

7. The method of claim 1, wherein the patient tissue is included in a pericardial space, the method including: deploying the catheter within the pericardial space.

8. The method of claim 1 including monitoring a cardiac biosignal via an electrode fixedly connected to the sheath and separate from the catheter.

9. The method of claim 1, wherein the patient tissue is included in a pericardial space, the method including repeatedly, without removing the catheter from the first lumen, both (a) ablating the patient tissue with the catheter; and (b) removing the patient fluid via the second lumen.

10. The method of claim 1 including stabilizing the sheath against the patient tissue by applying negative pressure to the first fenestration.

11. The method of claim 1, wherein the patient tissue is included in a pericardial space, the method including navigating the sheath within the a pericardial space based on applying negative pressure to the first fenestration.

12. The method of claim 1 including irrigating an area near the patient tissue and simultaneously performing: (a) the ablating the patient tissue with the catheter, (b) the removing the patient fluid via the second lumen, and (c) the irrigating the area near the patient tissue.

13. The method of claim 12 wherein the irrigating the area near the patient tissue includes irrigating the area near the patient tissue via a third lumen included in the sheath.

14. A method comprising:
providing a sheath having first and second lumens;
deploying a catheter within the first lumen but not the second lumen;
stabilizing the sheath against patient tissue by applying negative pressure to a fenestration included in a lateral wall of the sheath;
ablating the patient tissue with the catheter emerging from a distal end portion of the sheath; and
removing patient fluid via the second lumen while the catheter is deployed within the first lumen.

15. The method of claim 14 including stabilizing the sheath directly against the patient tissue by applying negative pressure to the fenestration to directly contact the sheath to the patient tissue;
wherein the catheter moves independently of the sheath.

16. The method of claim 14 including irrigating the patient tissue with a fluid that directly contacts an inner wall of the second lumen.

17. The method of claim 14 including irrigating the patient tissue via a third lumen included in the distal end portion of the sheath.

18. The method of claim 14, wherein the lateral wall couples the distal end portion of the sheath to a proximal end portion of the sheath and the lateral wall is orthogonal to the distal end portion.

* * * * *